(12) United States Patent
Boone et al.

(10) Patent No.: US 10,544,076 B1
(45) Date of Patent: Jan. 28, 2020

(54) METHOD OF MAKING A DIALDEYHDE

(71) Applicant: Eastman Chemical Company, Kingsport, TN (US)

(72) Inventors: Matthew Allen Boone, Kingsport, TN (US); William Christopher Ketchie, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/559,988

(22) Filed: Sep. 4, 2019

(51) Int. Cl.
C07C 45/58 (2006.01)

(52) U.S. Cl.
CPC .................... C07C 45/58 (2013.01)

(58) Field of Classification Search
CPC ....................................................... C07C 45/58
See application file for complete search history.

(56) References Cited

U.S. PATENT DOCUMENTS

| | | | |
|---|---|---|---|
| 2,578,724 | A | 12/1951 | Mertzweiller |
| 4,839,413 | A | 6/1989 | Kiehlbauch et al. |
| 4,927,876 | A | 5/1990 | Coogan et al. |
| 4,939,233 | A | 7/1990 | Jenkins et al. |
| 4,946,932 | A | 8/1990 | Jenkins |
| 5,137,961 | A | 8/1992 | Goos et al. |
| 5,247,040 | A | 9/1993 | Amick et al. |
| 5,296,530 | A | 3/1994 | Bors et al. |
| 5,484,849 | A | 1/1996 | Bors et al. |
| 6,451,380 | B1 | 9/2002 | Speece, Jr. et al. |
| 6,743,748 | B2 * | 6/2004 | Mizuno .................. B01J 23/002 502/254 |
| 7,208,545 | B1 | 4/2007 | Brunner et al. |
| 9,932,486 | B1 | 4/2018 | Cogar et al. |
| 2009/0076311 | A1 | 3/2009 | Sato et al. |
| 2012/0289721 | A1 | 11/2012 | End et al. |
| 2015/0239816 | A1 | 8/2015 | Zaragoza Doerwald et al. |

FOREIGN PATENT DOCUMENTS

| EP | 0 492 847 A2 | 7/1992 |
|---|---|---|
| WO | WO 2007/094922 A2 | 8/2007 |

OTHER PUBLICATIONS

Safa et al. 1,4-bis[2,2(trimethylsilyl) ethyenyl] benzene: Regioselective ring opening of its alpa, beta-epoxybis (silane) with some nucleophiles. Journal of Organic Chemistry, vol. 694, 1907-1911. (Year: 2009).*
Robinson et al. Epoxide ring-opening and Meinwald rearrangement reactions of epoxides catalyzed by mesoporous aluminosilicates. Org. Biomol. Chem., vol. 7, 2559-2564. (Year: 2009).*
Co-pending U.S. Appl. No. 16/559,842, filed Sep. 4, 2019; Boone.
Co-pending U.S. Appl. No. 16/559,871, filed Sep. 4, 2019; Boone.
Co-pending U.S. Appl. No. 16/559,887, filed Sep. 4, 2019; Boone.
Co-pending U.S. Appl. No. 16/559,912, filed Sep. 4, 2019; Boone.
Co-pending U.S. Appl. No. 16/559,897, filed Sep. 4, 2019; Boone.
Co-pending U.S. Appl. No. 16/559,880, filed Sep. 4, 2019; Boone et al.
Co-pending U.S. Appl. No. 16/559,859, filed Sep. 4, 2019; Boone et al.
Co-pending U.S. Appl. No. 16/560,146, filed Sep. 4, 2019; Boone et al.
Co-pending U.S. Appl. No. 16/560,161, filed Sep. 4, 2019; Boone et al.
Co-pending U.S. Appl. No. 16/559,977, filed Sep. 4, 2019; Boone.
ASTM D1544; Standard Test Method for Color of Transparent Liquids (Gardner Color Scale).
ASTM D2354-10$^{e1}$; Standard Test Method for Minimum Film Formation Temperature (MFFT) of Emulsion Vehicles.
ASTM D4946; Standard Test Method for Blocking Resistance of Architectural Paints.
ASTM D6886; Standard Test Method for Determination of the Weight Percent Individual Volatile Organic Compounds in Waterborne Air-Dry Coatings by Gas Chromatography.
Burczyk, B. et al.; "Relations between chemical structure and surface activity I: Synthesis and properties of aqueous solutions of acetals formed from aliphatic aldehydes and monoalkyl ethers of ethylene glycols;" Tenside Detergents; 15(2); 1978; pp. 68-71.
Burczyk, B. et al.; "Surface Properties of Selected Linear and Cyclic Acetals;" Tensioactivos: Biodegradabilidad, Fis.-Quim. Apl., Jorn. Com. Esp. Deterg.; 11$^{th}$; 1980; pp. 581-601.
Cohen, R. et al.; "Foam stabilizing properties of linear acetals containing oxyethylene units in their molecules;" Tenside Detergents; 18 (4); 1981; pp. 202-205.
Duchene, A. et al.; "Alxoxyméthyltributylétains précurseurs d'alcoxyméthyllithiums : application à la synthèse de monoéthers d'α-glycols et à l'homologation de cétones en aldéhydes;" Bulletin De La Societe Chimique De France; 1985; No. 5; pp. 787-792.
Getzkin, AJ. et al.; "Synthesis of Some Symmetrical Aldehyde Glycol Monoether Acetals;" Journal of the American Pharmaceutical Association, Scientific Edition; 49; 1960; pp. 746-750.
Kanno, T. et al.; "Oxygenation of Aromatic Vinyl Ethers. A Noticeable Formation of Epoxides and Reaction Mechanism;" Bull. Chem. Soc. Jpn.; 54; 1981; pp. 2330-2336.
Moszner, N. et al.; "Reaction behavior of monomeric β-ketoesters. 2. Synthesis, characterization and polymerization of methacrylate group containing enamines;" Polymer Bulletin; 32; pp. 419-426; (1994).

(Continued)

Primary Examiner — Sikarl A Witherspoon
(74) Attorney, Agent, or Firm — Matthew W. Smith

(57) ABSTRACT

We have discovered that a di-epoxide can be converted to a dialdehyde using an amorphous silica-alumina catalyst. The method comprises contacting a di-epoxide mixed in an organic solvent with a silica-alumina catalyst to form a solvent and dialdehyde reaction product mixture and separating said dialdehyde from said reaction mixture. The dialdehydes have utility as chemical intermediates, and particular utility in processes to make enol ether compounds which can be used in applications as plasticizers, diluents, wetting agents, coalescing aids and as intermediates in chemical processes.

6 Claims, No Drawings

(56) References Cited

OTHER PUBLICATIONS

Presidential Green Chemistry Challenge: 2005 Designing Greener Chemical Award; Archer Daniels Midland Company; Archer RC™: A Nonvolatile, Reactive Coalescent for the Reduction of VOCs in Latex Paints; United States Environmental Protection Agency; Accessed via the web on Jun. 6, 2018; https://www.epa.gov/greenchemistry/presidential-green-chemistry-challenge-2005-designing-greener-chemicals-award.

Smith, O.W. et al.; "New vinyl ester monomers for emulsion polymers;" Progress in Organic Coatings; 22; 1993; pp. 19-25.

Sokolowski, A. et al.; "Acetals and Ethers. Part IV*. Synthesis of Acetals from Aliphatic Aldehydes and Monoalkyl Ether of Ethylene Glycols;" Polish Journal of Chemistry (formerly Roczniki Chemii); 53(4); 1979; pp. 905-912.

Sokolowski, A. et al.; "Statistical Evaluation of the Influence of Linear Acetal Structures on Their Adsorption at the Aqueous Solution-Air Interface;" Comunicaciones presentadas a las XII Jornadas del Comite Espanol de la Detergencia; Asociacion De Investigacion De Detergentes, TENS; 1981; pp. 491-507.

* cited by examiner

METHOD OF MAKING A DIALDEYHDE

FIELD OF THE INVENTION

This application relates to chemistry generally. In particular, this application relates to a novel method of making dialdehydes from diepoxides.

BACKGROUND OF THE INVENTION

Mono-epoxide to mono-aldehyde rearrangements are well known in the chemical arts. However, di-epoxide rearrangement to di-aldehyde processes are less known. For example, common Lewis acids and Bronsted acids lead to oligomerization and the production of complex mixtures of products when a difunctional rearrangement is attempted.

Di-aldehydes are particularly useful as chemical intermediates to make material such as enol ethers It would be desirable to have an efficient process to make dialdehydes directly from diepoxides.

SUMMARY OF THE INVENTION

The Invention is set forth in the appended claims.

In one embodiment the invention is a method of making a dialdehyde comprising contacting a di-epoxide with a silica-alumina catalyst.

In another embodiment the invention is a method of making a dialdehyde comprising contacting a di-epoxide and an organic solvent with a silica-alumina catalyst to form a solvent and dialdehyde reaction mixture and. separating said dialdehyde from said reaction mixture.

DETAILED DESCRIPTION

Definitions

In this specification and in the claims that follow, reference will be made to a number of terms, which shall be defined to have the following meanings.

"Alcohol" means a chemical containing one or more hydroxyl groups.

"Aldehyde" means a chemical containing one or more —C(O)H groups.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise" provided above.

"Chosen from" as used herein can be used with "or" or "and." For example, Y is chosen from A, B, and C means Y can be individually A, B, or C. Alternatively, Y is chosen from A, B, or C means Y can be individually A, B, or C; or a combination of A and B, A and C, B and C, or A, B, and C.

Presented herein is a processes to directly convert a diepoxide to a dialdehyde via novel synthesis methods Mono-epoxide to mono-aldehyde rearrangements are well known. However, when attempting to extend scope to di-aldehyde to di-epoxide rearrangement, the chemistry options are far lacking. For example, common Lewis acids and Bronsted acids lead to oligomerization and the production of complex mixtures of products when a difunctional rearrangement was attempted. Conditions screened include tritylium tetrafluorborate, boron trifluoride, zinc chloride, methanesulfonic acid, solid supported acids (e.g. Amberlyst™ 15, Nafion™ NR50)—all of which led to complicated reaction mixtures. Other catalysts that have been screened include kaolinte, bentonite, Zeolite Y, acidic aluminum oxide, and silica gel. These conditions all resulted in no reaction. Kaolinite, bentonite, and Zeolite Y are characterized as alumina silicates yet do not possess catalytic activity towards the di-epoxide to dialdehyde transformation of this invention.

We have discovered that a di-epoxide can be directly and cleanly converted to the dialdehyde using an amorphous silica-alumina catalyst.

In one embodiment the method comprises:

a. contacting a di-epoxide mixed in an organic solvent with a silica-alumina catalyst to form a solvent and dialdehyde reaction product mixture; and b. separating said dialdehyde from said reaction mixture.

Di-epoxides suitable for the method include 1,3-bis(2-methyloxiran-2-yl)benzene, 1,4-bis(2-methyloxiran-2-yl) benzene, 1,3-di(oxiran-2-yl)benzene, 1,4-di(oxiran-2-yl) benzene 4,4'-bis(2-methyloxiran-2-yl)-1,1'-biphenyl, and 2,6-bis(2-methyloxiran-2-yl)naphthalene and mixtures thereof.

Preferred di-epoxides for the method include 1,3-bis(2-methyloxiran-2-yl)benzene, 1,4-bis(2-methyloxiran-2-yl) benzene.

Catalysts suitable for the method include silica-alumina Grade 135, amorphous silica-aluminas, and acid-washed bleaching earths.

Solvents suitable for the method include heptane, toluene, chlorobenzene, para-xylene, meta-xylene, ortho-xylene, ethyl acetate, acetonitrile, acetone, methyl ethyl ketone, methyl isobutyl ketone, and heptane and mixtures thereof.

Preferred solvents for the method are toluene, chlorobenzene, and xylenes.

EXAMPLES

Abbreviations mL is milliliter; hrs or h is hour(s); mm is millimeter; m is meter; GC is gas chromatography; ° C. is degree Celsius; min is minute; $t_R$ is retention time; g is gram; L is liter; μL is microliter; PSD is particle size distribution.

Example 1: Preparation of 2,2'(1,4-phenylene)dipropanal [3]

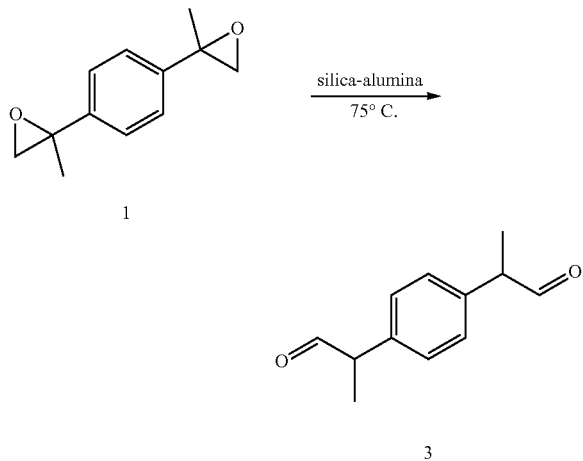

A solution of toluene (300 mL) and silica-alumina grade 135 (distributed by Sigma-Aldrich as an amorphous catalyst support, ca. 6.5% Al, PSD—100 mesh (99.3%)) (50 g) was heated to reflux in a 1 L 4-neck round-bottom flask fitted with an overhead stirrer, thermocouple, and a Dean-Stark trap. After 4 hrs, ca. 5 mL of water was collected. The mixture was then cooled to 75° C., whereupon 1,4-bis(2-methyloxiran-2-yl)benzene [1] (100 g) was added in 10 g portions over the course of 1 hr. After the last addition, GC indicated complete conversion of 1 to 2,2'-(1,4-phenylene) dipropanal [3]. Heating was stopped, and the mixture was allowed to cool to ambient temperature. The silica-alumina was removed via filtration through a 1-micron glass-fiber disc. The filtrate was concentrated under reduced pressure using a rotary evaporator. The crude material was then Kugelrohr—distilled at 1 mm Hg/150° C. to afford pure 2,2'-(1,4-phenylene)dipropanal [3]. GC-MS $t_R$: 14.47 min (Exact mass: 190.10 m/z, found: 190.1 m/z).

Example 2: Preparation of 2,2'(1,3-phenylene)dipropanal [6]

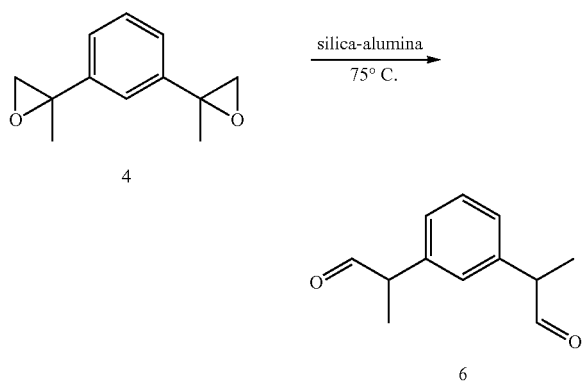

A solution of toluene (300 mL) and silica-alumina grade 135 (distributed by Sigma-Aldrich as an amorphous catalyst support, ca. 6.5% Al, PSD—100 mesh (99.3%)) (50 g) was heated to reflux in a 1 L 4-neck round-bottom flask fitted with an overhead stirrer, thermocouple, and a Dean-Stark trap. After 4 hrs, ca. 5 mL of water was collected. The mixture was then cooled to 75° C., whereupon 1,3-bis(2-methyloxiran-2-yl)benzene [4] (100 g) was added dropwise over the course of 1 hr. After the last addition, GC indicated complete conversion of 4 to 2,2'-(1,3-phenylene)dipropanal [3]. Heating was stopped, and the mixture was allowed to cool to ambient temperature. The silica-alumina was removed via filtration through a 1-micron glass-fiber disc (the recovered solid was washed with EtOAc and then dried in a 50° C. oven—the material was recycled and subjected to the reaction conditions again, showing no appreciable loss of activity). The filtrate was concentrated under reduced pressure using a rotary evaporator. The crude material was then Kugelrohr—distilled at 1 mm Hg/150° C. to afford pure 2,2'-(1,3-phenylene)dipropanal [6]. GC-MS $t_R$: 14.47 min (Exact mass: 190.10 m/z, found: 190.1 m/z).

This procedure was repeated at 100° C. with 100 g of diepoxide [4], 300 mL of toluene, and 25 g of Si—Al Grade 135 with no change in conversion or appearance of change in activity.

This procedure was repeated at 100° C. with 100 g of diepoxide [4], 400 mL of toluene, and 10 g of Si—Al Grade 135 with no change in conversion or appearance of change in activity.

The procedure was repeated at 100° C. with 100 g of diepoxide [4], 400 mL of toluene, and 5 g of Si—Al Grade 135 with no change in conversion or appearance of change in activity.

GC-MS Instrument Parameters—Agilent 6890N GC with Agilent 5975B VL MSD

Sample Prep: 100 µL sample diluted to 1 mL with toluene; Column: DB-5 30 m×0.25 mm×0.25 µm; Oven Ramp: 0-4.5 mins at 40° C.; Ramp 20 C/min to 280 C, Hold 53.5 mins; Injector: Temperature—250° C.; Split Flow—65 mL/min; Carrier Flow Rate—1.3 mL/min; Volume—1.0 µL; MS: Transfer Line—280° C.; Ion Source Temp—230° C.; Mass Range—34-700 amu.

The invention has been described in detail with reference to the embodiments disclosed herein, but it will be understood that variations and modifications can be effected within the spirit and scope of the invention.

We claim:

1. A method of making a dialdehyde comprising contacting a di-epoxide with a silica-alumina catalyst.

2. A method of making a dialdehyde comprising:
   a. contacting a di-epoxide and an organic solvent with a silica-alumina catalyst to form a solvent and dialdehyde reaction mixture; and
   b. separating said dialdehyde from said reaction mixture.

3. The method of claim 2 wherein said diepoxide is selected from the group comprising 1,3-bis(2-methyloxiran-2-yl)benzene, 1,4-bis(2-methyloxiran-2-yl)benzene, 1,3-di(oxiran-2-yl)benzene, 1,4-di(oxiran-2-yl)benzene 4,4'-bis(2-methyloxiran-2-yl)-1,1'-biphenyl, and 2,6-bis(2-methyloxiran-2-yl)naphthalene and mixtures thereof.

4. The method of claim 2 wherein said di-epoxides is 1,3-bis(2-methyloxiran-2-yl)benzene, 1,4-bis(2-methyloxiran-2-yl)benzene.

5. The method of claim 2 wherein said silica alumina catalyst is selected from the group consisting of silica-alumina Grade 135, amorphous silica-aluminas, and acid-washed bleaching earths.

6. The method of claim 2 wherein said solvent is selected from the group consisting of heptane, toluene, chlorobenzene, para-xylene, meta-xylene, ortho-xylene, ethyl acetate, acetonitrile, acetone, methyl ethyl ketone, methyl isobutyl ketone, and heptane and mixtures thereof.

* * * * *